United States Patent
Wilson et al.

[11] Patent Number: 6,019,778
[45] Date of Patent: Feb. 1, 2000

[54] DELIVERY APPARATUS FOR A SELF-EXPANDING STENT

[75] Inventors: David J. Wilson, Ft. Lauderdale; Kirk Johnson, Weston, both of Fla.

[73] Assignee: Cordis Corporation, Miami Lakes, Fla.

[*] Notice: This patent issued on a continued prosecution application filed under 37 CFR 1.53(d), and is subject to the twenty year patent term provisions of 35 U.S.C. 154(a)(2).

[21] Appl. No.: 09/042,276

[22] Filed: Mar. 13, 1998

[51] Int. Cl.$^7$ .................................................. A61M 29/00
[52] U.S. Cl. .................................. 606/198; 623/1; 623/12
[58] Field of Search .............................. 606/1, 108, 191, 606/194, 198, 200; 623/1, 12; 898/898; 604/96, 282

[56] References Cited

U.S. PATENT DOCUMENTS

| | | |
|---|---|---|
| 3,485,234 | 12/1969 | Stevens . |
| 3,585,707 | 6/1971 | Stevens . |
| 3,612,058 | 10/1971 | Ackerman . |
| 4,516,972 | 5/1985 | Samson . |
| 4,580,568 | 4/1986 | Gianturco . |
| 4,665,771 | 5/1987 | Mitchell . |
| 4,665,905 | 5/1987 | Brown . |
| 4,665,918 | 5/1987 | Garza . |
| 4,676,229 | 6/1987 | Krasnicki . |
| 4,705,511 | 11/1987 | Kocak . |
| 4,732,152 | 3/1988 | Wallsten . |
| 4,733,665 | 3/1988 | Palmaz . |
| 4,768,507 | 9/1988 | Fischell . |
| 4,817,613 | 4/1989 | Jaraczewski . |
| 4,842,590 | 6/1989 | Tanabe . |
| 4,875,468 | 10/1989 | Krauter . |
| 4,898,591 | 2/1990 | Jang . |
| 4,925,445 | 5/1990 | Sakamoto . |
| 4,954,126 | 9/1990 | Wallsten . |
| 4,998,539 | 3/1991 | Delsanti . |
| 5,026,377 | 6/1991 | Burton . |
| 5,045,072 | 9/1991 | Castillo . |
| 5,057,092 | 10/1991 | Webster . |
| 5,069,674 | 12/1991 | Fearnot . |
| 5,089,005 | 2/1992 | Harada . |
| 5,160,341 | 11/1992 | Brenneman . |
| 5,190,520 | 3/1993 | Fenton . |
| 5,201,901 | 4/1993 | Harada . |
| 5,217,440 | 6/1993 | Frassica . |
| 5,221,270 | 6/1993 | Parker . |
| 5,221,372 | 6/1993 | Olson . |
| 5,254,107 | 10/1993 | Soltesz . |
| 5,279,596 | 1/1994 | Castaneda . |
| 5,290,295 | 3/1994 | Querals . |
| 5,306,252 | 4/1994 | Yutori . |
| 5,415,664 | 5/1995 | Pinchuk . |
| 5,449,373 | 9/1995 | Pinchasik . |
| 5,480,423 | 1/1996 | Ravenscroft . |
| 5,514,154 | 5/1996 | Lau . |
| 5,534,007 | 7/1996 | St. Germain . |
| 5,538,510 | 7/1996 | Fontrirroche . |
| 5,554,139 | 9/1996 | Okajima .................................. 604/282 |
| 5,562,641 | 10/1996 | Flomenblit . |
| 5,569,295 | 10/1996 | Lam . |
| 5,571,170 | 11/1996 | Palmaz . |
| 5,591,197 | 1/1997 | Orth . |
| 5,603,698 | 2/1997 | Roberts . |
| 5,603,721 | 2/1997 | Lau . |
| 5,649,952 | 7/1997 | Lam . |
| 5,674,208 | 10/1997 | Berg . |
| 5,690,644 | 11/1997 | Yurek . |
| 5,695,499 | 12/1997 | Helgerson . |
| 5,697,971 | 12/1997 | Fischell . |
| 5,700,269 | 12/1997 | Pinchuk et al. .......................... 606/198 |
| 5,702,418 | 12/1997 | Ravenscroft . |
| 5,704,926 | 1/1998 | Sutton . |
| 5,707,376 | 1/1998 | Kavteladze . |
| 5,728,158 | 3/1998 | Lau . |
| 5,735,859 | 4/1998 | Fischell . |
| 5,735,893 | 4/1998 | Lau . |
| 5,755,781 | 5/1998 | Jayaraman . |
| 5,776,140 | 7/1998 | Cottone .................................. 606/198 |
| B1 4,954,126 | 5/1996 | Wallsten . |

FOREIGN PATENT DOCUMENTS

| | | |
|---|---|---|
| 0 177 330 | 1/1985 | European Pat. Off. . |
| WO 96/32078 | 10/1996 | WIPO . |

*Primary Examiner*—Michael Buiz
*Assistant Examiner*—William W. Lewis
*Attorney, Agent, or Firm*—Dean Garner

[57] ABSTRACT

In accordance with the present invention there is provided a delivery apparatus for a self-expanding stent. The apparatus includes an outer sheath, which is an elongated tubular member having distal and proximal ends. The outer sheath is made from an outer polymeric layer, an inner polymeric layer, and a braided reinforcing layer between the inner and outer layers. The reinforcing layer is more rigid than the inner and outer layers. The apparatus further includes an inner shaft located coaxially within the outer sheath. The shaft has a distal end, extending distal to the distal end of the sheath, and a proximal end, extending proximal to the proximal end of the sheath. The shaft further includes a stop attached thereto. The stop is proximal to the distal end of the sheath. Lastly, the apparatus includes a self-expanding stent located within the sheath. The stent makes frictional contact with the inner layer of the sheath. The stent is located between the stop and the distal end of the sheath, with a portion of the shaft disposed coaxially within a lumen of the stent. The stent makes contact with the stop during deployment of the stent.

31 Claims, 4 Drawing Sheets

DELIVERY APPARATUS FOR A SELF-EXPANDING STENT

FIELD OF THE INVENTION

The present invention relates to an expandable intraluminal grafts ("stents") for use within a body passageway or duct which are particularly useful for repairing blood vessels narrowed or occluded by disease. The present invention relates even further to systems for delivering such stents.

BACKGROUND OF THE INVENTION

Percutaneous transluminal coronary angioplasty (PTCA) is a therapeutic medical procedure used to increase blood flow through the coronary artery and can often be used as an alternative to coronary by-pass surgery. In this procedure, the angioplasty balloon is inflated within the stenosed vessel, or body passageway, in order to shear and disrupt the wall components of the vessel to obtain an enlarged lumen. With respect to arterial stenosed lesions, the relatively incompressible plaque remains unaltered, while the more elastic medial and adventitial layers of the body passageway stretch around the plaque. This process produces dissection, or a splitting and tearing, of the body passageway wall layers, wherein the intima, or internal surface of the artery or body passageway, suffers fissuring. This dissection forms a "flap" of underlying tissue which may reduce the blood flow through the lumen, or block the lumen. Typically, the distending intraluminal pressure within the body passageway can hold the disrupted layer, or flap, in place. If the intimal flap created by the balloon dilation procedure is not maintained in place against the expanded intima, the intimal flap can fold down into the lumen and close off the lumen, or may even become detached and enter the body passageway. When the intimal flap closes off the body passageway, immediate surgery is necessary to correct this problem.

Recently, transluminal prostheses have been widely used in the medical arts for implantation in blood vessels, biliary ducts, or other similar organs of the living body. These prostheses are commonly known as stents and are used to maintain, open, or dilate tubular structures. An example of a commonly used stent is given in U.S. Pat. No. 4,733,665 filed by Palmaz on Nov. 7, 1985, which is hereby incorporated herein by reference. Such stents are often referred to as balloon expandable stents. Typically the stent is made from a solid tube of stainless steel. Thereafter, a series of cuts are made in the wall of the stent. The stent has a first smaller diameter which permits the stent to be delivered through the human vasculature by being crimped onto a balloon catheter. The stent also has a second, expanded diameter, upon the application, by the balloon catheter, from the interior of the tubular shaped member of a radially, outwardly extending.

However, such stents are often impractical for use in some vessels such as the carotid artery. The carotid artery is easily accessible from the exterior of the human body, and is often visible by looking at ones neck. A patient having a balloon expandable stent made from stainless steel or the like, placed in their carotid artery might be susceptible to sever injury through day to day activity. A sufficient force placed on the patients neck, such as by falling, could cause the stent to collapse, resulting in injury to the patient. In order to prevent this, self expanding stents have been proposed for use in such vessels. Self expanding stents act like springs and will recover to their expanded or implanted configuration after being (crushed.

One type of self-expanding stent is disclosed in U.S. Pat. No. 4,665,771, which stent has a radially and axially flexible, elastic tubular body with a predetermined diameter that is variable under axial movement of ends of the body relative to each other and which is composed of a plurality of individually rigid but flexible and elastic thread elements defining a radially self-expanding helix. This type of stent is known in the art as a "braided stent" and is so designated herein. Placement of such stents in a body vessel can be achieved by a device which comprise an outer catheter for holding the stent at its distal end, and an inner piston which pushes the stent forward once it is in position.

Other types of self-expanding stents use alloys such as Nitinol (Ni—Ti alloy) which have shape memory and/or superelastic characteristics in medical devices which are designed to be inserted into a patient's body. The shape memory characteristics allow the devices to be deformed to facilitate their insertion into a body lumen or cavity and then be heated within the body so that the device returns to its original shape. Superelastic characteristics on the other hand generally allow the metal to be deformed and restrained in the deformed condition to facilitate the insertion of the medical device containing the metal into a patient's body, with such deformation causing the phase transformation. Once within the body lumen the restraint on the superelastic member can be removed, thereby reducing the stress herein so that the superelastic member can return to its original un-deformed shape by the transformation back to the original phase.

Alloys having shape memory/superelastic characteristics generally have at least two phases. These phases are a martensite phase, which has a relatively low tensile strength and which is stable at relatively low temperatures, and an austenite phase, which has a relatively high tensile strength and which is stable at temperatures higher than the martensite phase.

When stress is applied to a specimen of a metal such as Nitinol exhibiting superelastic characteristics at a temperature above which the austenite is stable (i.e. the temperature at which the transformation of martensite phase to the austenite phase is complete), the specimen deforms elastically until it reaches a particular stress level where the alloy then undergoes a stress-induced phase transformation from the austenite phase to the martensite phase. As the phase transformation proceeds, the alloy undergoes significant increases in strain but with little or no corresponding increases in stress. The strain increases while the stress remains essentially constant until the transformation of the austenite phase to the martensite phase is complete. Thereafter, further increase in stress are necessary to cause further deformation. The martensitic metal first deforms elastically upon the application of additional stress and then plastically with permanent residual deformation.

If the load on the specimen is removed before any permanent deformation has occurred, the martensitic specimen will elastically recover and transform back to the austenite phase. The reduction in stress first causes a decrease in strain. As stress reduction reaches the level at which the martensite phase transforms back into the austenite phase, the stress level in the specimen will remain essentially constant (but substantially less than the constant stress level at which the austenite transforms to the martensite) until the transformation back to the austenite phase is complete, i.e. there is significant recovery in strain with only negligible corresponding stress reduction. After the transformation back to austenite is complete, further stress reduction results in elastic strain reduction. This ability to incur significant strain at relatively constant stress upon the application of a load and to recover from the deformation upon the removal of the load is commonly referred to as superelasticity or pseudoelasticity. It is this property of the material which makes it useful in manufacturing tube cut self-expanding stents. The prior art makes reference to the use of metal alloys having superelastic characteristics in medical devices which are intended to be inserted or otherwise used within a patient's body. See for example, U.S. Pat. No. 4,665,905 (Jervis) and U.S. Pat. No. 4,925,445 (Sakamoto et al.).

Designing delivery systems for delivering self-expanding stents has proven difficult. One example of a prior art self-expanding stent delivery system is shown in U.S. Pat. No. 4,580,568 I issued to Gianturco on Apr. 8, 1986. This reference discloses a delivery apparatus which uses a hollow sheath, like a catheter. The sheath is inserted into a body vessel and navigated therethrough so that its distal end is adjacent the target site. The stent is then compressed to a smaller diameter and loaded into the sheath at the sheath's proximal end. A cylindrical flat end pusher, having a diameter almost equal to the inside diameter of the sheath is inserted into the sheath behind the stent. The pusher is then used to push the stent from the proximal end of the sheath to the distal end of the sheath. Once the stent is at the distal end of the sheath, the sheath is pulled back, while the pusher remain stationary, thereby exposing the stent and expanding it within the vessel.

However, delivering the stent through the entire length of the catheter can cause many problems, including possible damage to a vessel or the stent during its travel. In addition, it is often difficult to design a pusher having enough flexibility to navigate through the catheter, but also enough stiffness to push the stent out of the catheter. Therefore, it was discovered that pre-loading the stent into the distal and of the catheter, and then delivering the catheter through the vessel to the target site may be a better approach. In order to ensure proper placement of the stent within catheter, it is often preferred that the stent be pre-loaded at the manufacturing site. Except this in itself has posed some problems. Because the catheter exerts a significant force on the self expanding stent which keeps it from expanding, the stent may tend to become imbedded within the inner wall of the catheter. When this happens, the catheter has difficulty sliding over the stent during delivery. This situation can result in the stent becoming stuck inside the catheter, or could damage the stent during delivery.

Another example of a prior art self-expanding stent delivery system is given in U.S. Pat. No. 4,732,152 issued to Wallsten et al. on Mar. 22, 1988. This patent discloses a probe or catheter having a self-expanding stent pre-loaded into its distal end. The stent is first placed within a flexible hose and compressed before it is loaded into the catheter. When the stent is at the delivery site the catheter and hose are withdrawn over the stent so that it can expand within the vessel. However, withdrawing the flexible hose over the stent during expansion could also cause damage to the stent.

Therefore, there has been a need for a self-expanding stent delivery system which overcomes the above referenced problems associated with prior art delivery systems. Specifically, there has been a need for a self-expanding stent delivery system wherein the stent is loaded at the distal end of a catheter and wherein the catheter effectively resists the stent from imbedding itself therein. The present invention provides such a delivery device.

SUMMARY OF THE INVENTION

In accordance with the present invention there is provided a delivery apparatus for a self-expanding stent. The apparatus includes an outer sheath, which is an elongated tubular member having distal and proximal ends. The outer sheath is made from an outer polymeric layer, an inner polymeric layer, and a braided reinforcing layer between the inner and outer layers. The reinforcing layer is more rigid than the inner and outer layers. The apparatus further includes an inner shaft located coaxially within the outer sheath. The shaft has a distal end, extending distal to the distal end of the sheath, and a proximal end, extending proximal to the proximal end of the sheath. The shaft further includes a stop attached thereto. The stop is proximal to the distal end of the sheath. Lastly, the apparatus includes a self-expanding stent located within the sheath. The stent makes frictional contact with the inner layer of the sheath. The stent is located between the stop and the distal end of the sheath, with a portion of the shaft disposed coaxially within a lumen of the stent. The stent makes contact with the stop during deployment of the stent.

BRIEF DESCRIPTION OF DRAWINGS

The foregoing and other aspects of the present invention will best be appreciated with reference to the detailed description of the invention in conjunction with the accompanying drawings, wherein.

DETAILED DESCRIPTION OF THE INVENTION

Figure 1:
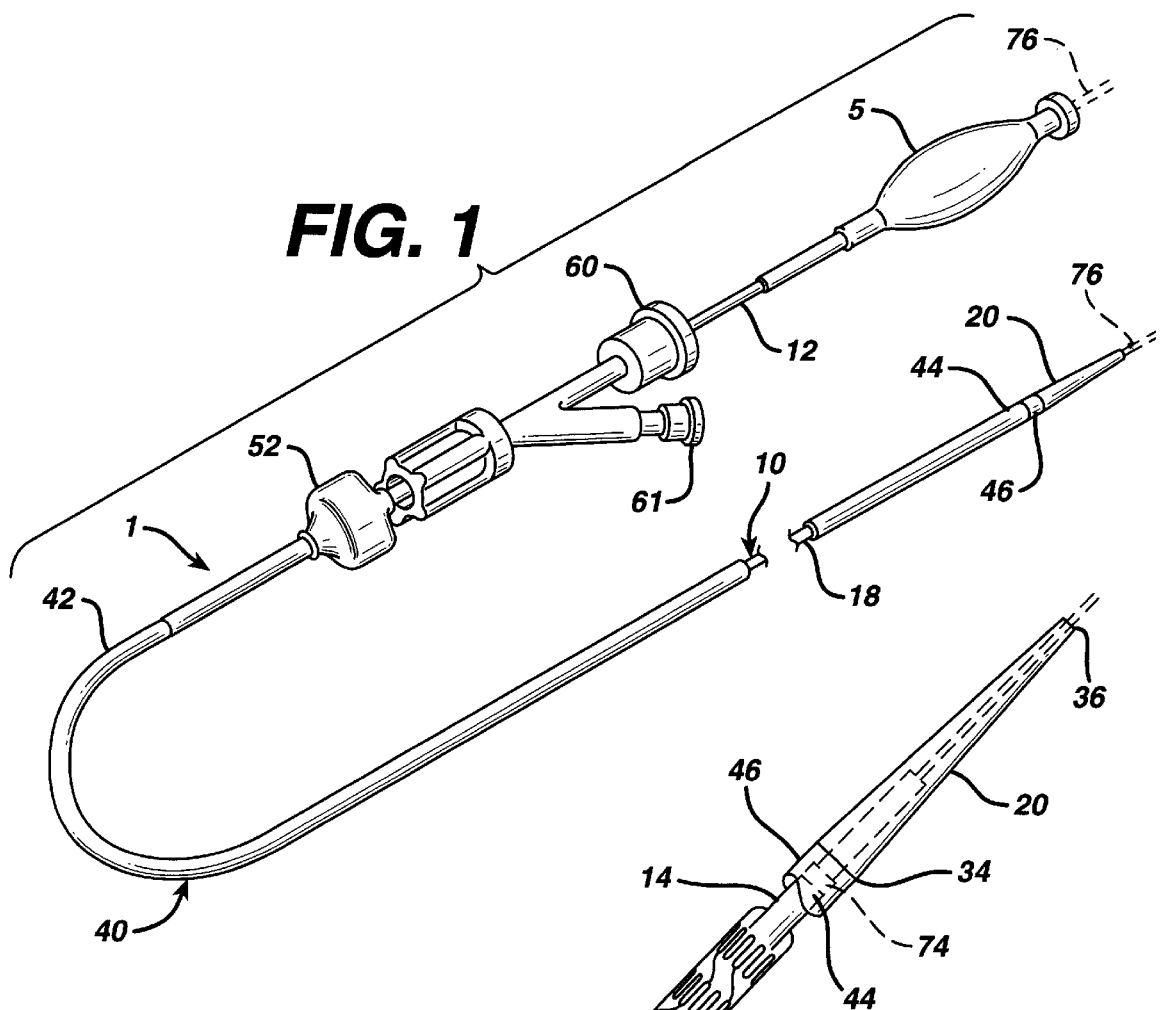
FIG. 1 is a simplified partial cross-sectional view of a stent delivery apparatus having a stent loaded therein, which can be used with a stent made in accordance with the present invention.
Figure 2:
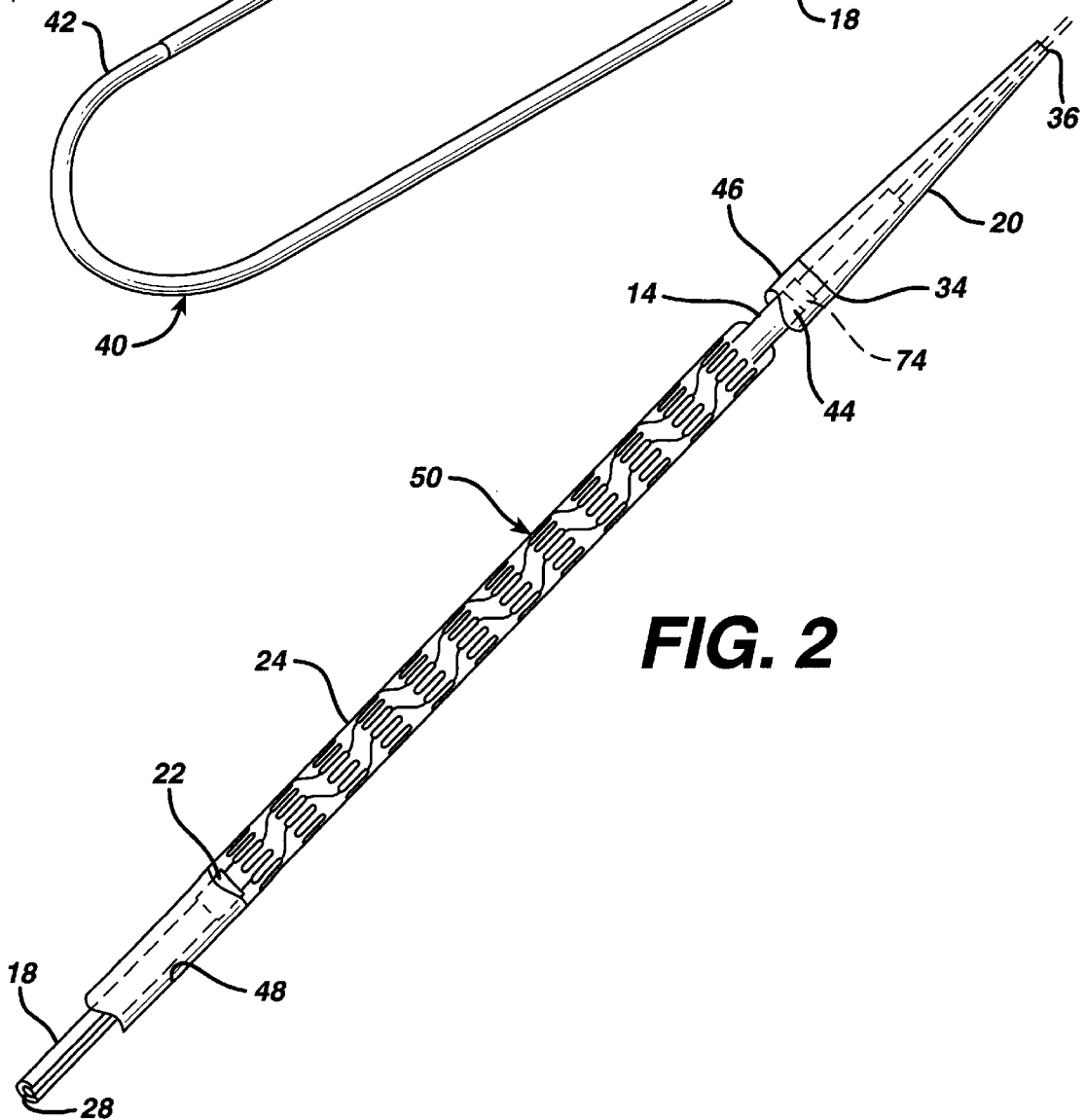
FIG. 2 is a view similar to that of FIG. 1 but showing an enlarged view of the distal end of the apparatus.
Figure 3:
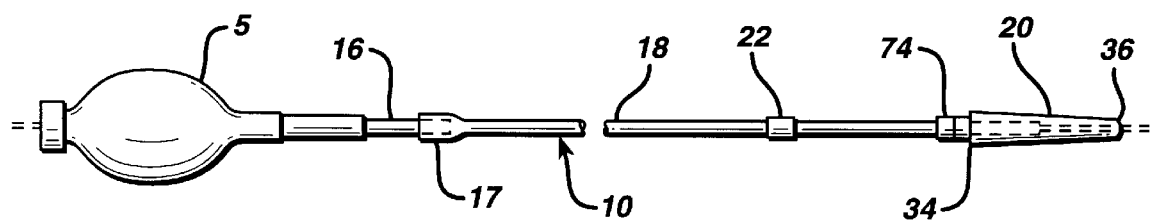
FIG. 3 is a perspective view of the inner shaft configuration without the outer sheath.

Referring now to the figures wherein like numerals indicate the same element throughout the views, there is shown in FIGS. 1 and 2 a self-expanding stent delivery apparatus 1 made in accordance with the present invention. Apparatus 1 comprises inner and outer coaxial tubes. The inner tube is called the shaft 10 and the outer tube is called the sheath 40. Shaft 10 has proximal and distal ends 12 and 14 respectively. The proximal end 12 of the shaft has a luer lock hub 5 attached thereto. As shown in FIG. 3, shaft 10 has a proximal portion 16 which is preferably made from a relatively stiff material such as stainless steel, Nitinol, or any other suitable material known to those of ordinary skill in the art. Shaft 10 also includes a distal portion 18 which is preferably made from a co-extrusion high density polyethylene for the inner portion and polyamide for the outer portion. Other suitable materials for distal portion 18 known to those of ordinary skill in the art include polyurethane, polyimide, PEEK®, or Nitinol. These materials may be utilized as single or multi-layer structures, and may also include reinforcement wires, braid wires, coils, filiments or the like. The two portions are joined together at joint 17 by any number of means known to those of ordinary skill in the art including heat fusing, adhesive bonding, chemical bonding or mechanical attachment. As will become apparent when describing the use of the apparatus, the stainless steel proximal end 16 gives the shaft the necessary rigidity or stiffness it needs to effectively push out the stent, while the distal portion 18 provides the necessary combination of flexibility, to navigate tortuous vessels, and column strength to effectively push out the stent.

Figure 4:
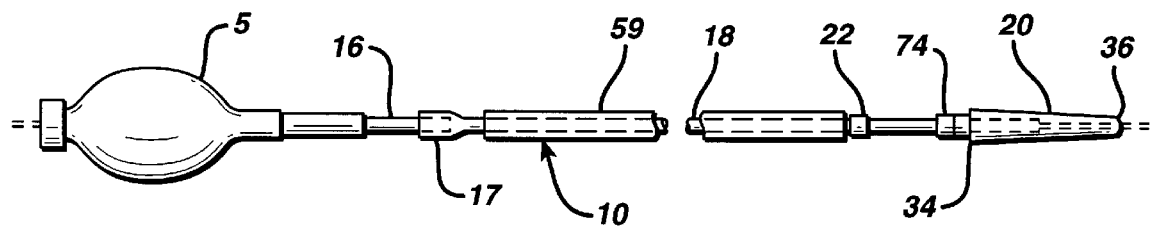
FIG. 4 is a view of the inner shaft configuration similar to that of FIG. 3 with a reinforcing sleeve attached.

As shown in FIG. 4, a reinforcing sleeve 59 can be attached to the inner shaft 10 to provide increased column strength for stent deployment. The sleeve is attached to shaft 10 preferably by any number of means known to those of ordinary skill in the art including heat fusing, adhesive bonding, chemical bonding or mechanical attachment. The sleeve is attached to portion 18 of shaft 10 at a location distal to joint 17 and at a location proximal to stop 22. The sleeve preferably does not make frictional contact with outer sheath 40. The space between inner shaft 10 and outer sheath 40 can be flushed prior to the clinical procedure to expel air with a syringe injection of fluid via Luer port 61 of Tuohy Borst valve 60.

The distal portion 14 of the shaft 10 has a distal tip 20 attached thereto. Distal tip 20 can be made from any number of materials known in the art including polyamide, polyurethane, polytetrafluoroethylene, and polyethylene including multi-layer or single layer structures. The distal tip 20 has a proximal end 34 whose diameter is substantially the same as the outer diameter of the sheath 40. The distal tip tapers to a smaller diameter from its proximal end 34 to its distal end 36, wherein the distal end 36 of the distal tip has a diameter smaller than the inner diameter of the sheath. Tip 20 helps to prevent blood from entering the sheath 40 as the apparatus 1 is being navigated through the body vessels. Attached to distal portion 14 of shaft 10 is a stop 22 which is proximal to the distal tip 20 and stent 50. Stop 22 can be made from any number of materials known in the art, including stainless steel, and is even more preferably made from a highly radiopaque material such as platinum, gold tantalum, or radiopaque filled polymer. The stop is attached to shaft 10 by mechanical means, adhesive bonding or any other method known to those skilled in the art. The apparatus 1 may include the reinforcing sleeve on shaft 10 as depicted in FIG. 3. In that case, the stop 22 can either be positively attached to shaft 10 at a position distal to the distal end of reinforcing sleeve 59 or can be free floating on shaft 10 at a position distal to but in contact with the distal end of reinforcing sleeve 59. Preferably, the diameter of stop 22 is large enough to make sufficient contact with the loaded stent 50 at its end 181 or 182 (FIG. 5) without making frictional contact with the inner layer 48 of the outer sheath 40. As will be explained later herein, stop 22 helps to push the stent out of the sheath during deployment, by preventing the stent from migrating proximally within the sheath 40 during retraction for stent deployment. During deployment, the outer sheath 40 is moved in a proximal direction relative to the stationary inner shaft 10. The radiopaque stop 22 also aides in stent positioning within the target lesion for deployment within the vessel as will be described herein.

A stent bed 24 is defined as being that portion of the shaft between the distal tip 20 and the stop 22. The stent bed 24 and the stent 50 are coaxial so that the portion of shaft 18 comprising the stent bed 24 is located within the lumen of stent 50. The stent bed 24 makes minimal contact with stent 50 because of the space which exists between the inner shaft 10 and the outer sheath 40. As the stent is subjected to temperatures at the austenite phase transformation it attempts to recover to its programmed shape by moving outwardly in a radial direction within the sheath. The outer sheath 40 constrains the stent as will be explained later herein.

Distal to the distal end of the loaded stent 50 attached to the inner shaft 10 is a radiopaque marker 74 which can be made of platinum, iridium coated platinum, gold, tantalum, stainless steel or any other suitable material known in the art. Lastly, shaft 10 has a guidewire lumen 28 extending along its length, where the guidewire enters through the guidewire hub 5 and exits through its distal tip 20. This allows the shaft 10 to receive a guidewire 76 much in the same way that a balloon angioplastly catheter receives a guidewire. Such guidewires are well known in the art and help to guide catheters and other medical devices through the vasculature of the body.

Sheath 40 is preferably a polymeric catheter and has a proximal end 42 terminating at a Luer hub 52. Sheath 40 also has a distal end 44 which terminates at the proximal end 34 of distal tip 20 of the shaft 18, when the stent 50 is in its fully un-deployed position as shown in the figures. The distal end 44 of sheath 40 includes a radiopaque marker band 74 disposed along its outer surface. As will be explained below, the stent is fully deployed when the marker band 46 is proximal to radiopaque stop 22, thus indicating to the physician that it is now safe to remove the apparatus 1 from the body.

Figure 6:
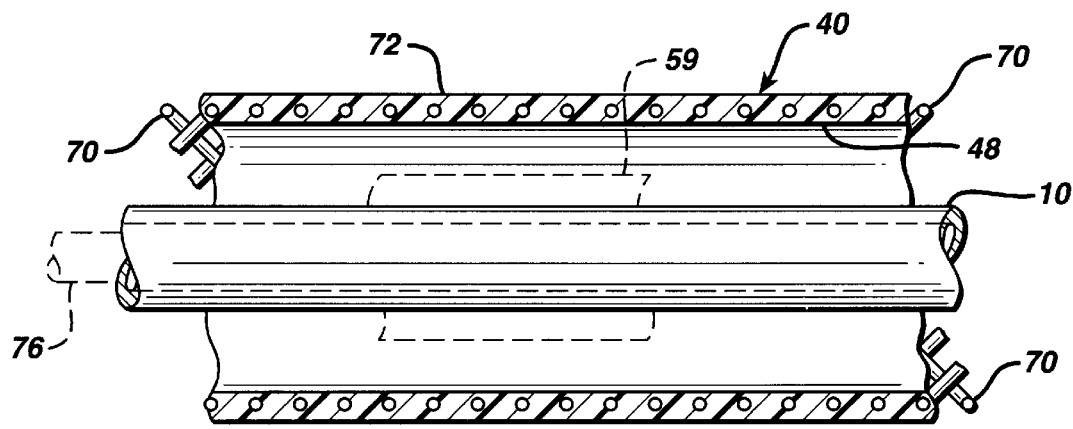
FIG. 6 is a partial cross-sectional view of the inner shaft, reinforcing sleeve, and multi-layered outer sheath.

As stated above, earlier self-expanding delivery systems had problems with the stent becoming embedded within the sheath or catheter in which it is disposed. By referring to FIG. 6, one can see how the present invention solves this problem. Sheath 40 preferably comprises an outer polymer, preferably nylon, layer 72 and an inner polymer, preferably polytetrafluroethylene, layer 48. Other suitable polymers for the inner and outer layers 72 and 48 include any suitable material known to those skilled in the art including polyethylene or polyamide. Positioned between outer and inner layers 72 and 48, respectively, is a wire reinforcing layer 70, which is preferably a braided wire. Braided reinforcing layer 70 is preferably made from stainless steel. The use of braiding reinforcing layers in other types of medical devices can be found in U.S. Pat. No. 3,585,707 issued to Stevens on Jun. 22, 1971, U.S. Pat. No. 5,045,072 issued to Castillo et al. on Sep. 3, 1991, and U.S. Pat. No. 5,254,107 issued to Soltesz on Oct. 19, 1993, all of which are hereby incorporated herein by reference.

Sheath 40 is a composite structure incorporating an inner polytetrafluoroethylene layer 48, an outer polyamide layer 72, and a middle stainless steel braid wire layer 70. The outer sheath 40 can incorporate a single outer polyamide layer 72 from proximal 42 to distal 44 or can be a series of fused transitions decreasing in material durometer from proximal 42 to distal 44 along outer layer 72 of sheath 40. The inclusion of transitions of varying material durometers can effectively enhance the catheter performance as it is pushed over the guidewire 76 through the vascular anatomy. The flexibility of the delivery system from proximal 42 to distal 44 of sheath 40 can improve the manner in which the system tracks over the guidewire 76.

Layers 48, 70, and 72 of sheath 40 collectively enhance stent 50 deployment. Layers 48 and 70 help to prevent the stent 50 from becoming too imbedded into sheath 40, prior to stent deployment. The braid layer 70 provides radial support to inner layer 48 creating sufficient resistance to the outward radial force of stent 50 within sheath 40. Inner layer 48 also provides a low coefficient of friction surface to reduce the forces required to deploy the stent 50. In addition to the above mentioned benefit, layer 70 offers many other advantages. Layer 70 gives the sheath better pushability, the ability to transmit a force applied by the physician at a proximal location 42 on sheath 40 to the distal tip 20, which aids in navigation across tight stenotic lesions within the vascular anatomy. Layer 70 also gives the sheath better resistance to elongation and necking as a result of tensile loading during sheath retraction for stent deployment. The configuration of braid layer 70 can be changed to change system performance. This is achieved by changing the pitch of the braid, the shape of the individual braidwires, the number of braidwires, and the braid wire diameter. Additionally, coils could be incorporated similarly to layer 70 of sheath 40 to minimize stent imbedment and enhance system flexibility. Use of coils in other types of catheters can be found in U.S. Pat. No. 5,279,596 issued to Castaneda et al. on Jan. 18, 1994, which is hereby incorporated herein by reference.

Prior art self-expanding stent delivery systems did not use braid layers and there may be many reasons why others have not tried this. Because of the size of most self-expanding stents are quite large, as compared to balloon expandable coronary stents, the diameters of the delivery devices had to be large as well. However, it is always advantageous to have catheters or delivery systems which are as small as possible. This is so the devices can reach into smaller vessels, and so that less trauma is caused to the patient. Thus others would have been led away from using such a layer. However, it has been found that even a very thin braid layer in a stent delivery apparatus offers such an advantage, that any incremental increase in the size of the catheter is worth it.

FIGS. 1 and 2 show the stent 50 as being in its fully un-deployed position. This is the position the stent is in when the apparatus 1 is inserted into the vasculature and its distal end is navigated to a target site. Stent 50 is disposed around the stent bed 24 and at the distal end 44 of sheath 40. The distal tip 20 of the shaft 10 is distal to the distal end 44 of the sheath 40. The stent 50 is in a compressed state and makes frictional contact with the inner surface 48 of the sheath 40.

When being inserted into a patient, sheath 40 and shaft 10 are locked together at their proximal ends by a Tuohy Borst valve 60. This prevents any sliding movement between the shaft and sheath which could result in a premature deployment or partial deployment of the stent. When the stent 50 reaches its target site and is ready for deployment, the Tuohy Borst valve 60 is opened so that the sheath 40 and shaft 10 are no longer locked together.

Figure 7:
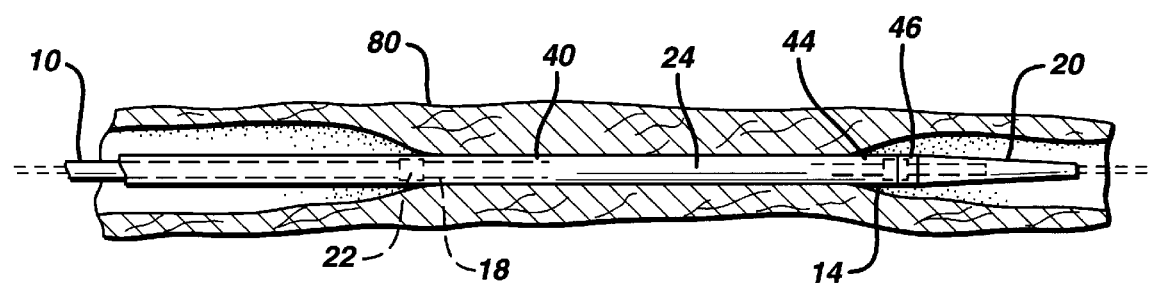
FIGS. 7 through 10 are partial cross-sectional views of the apparatus of the present invention showing the deployment of the self expanding stent within the vasculature.
Figure 8:
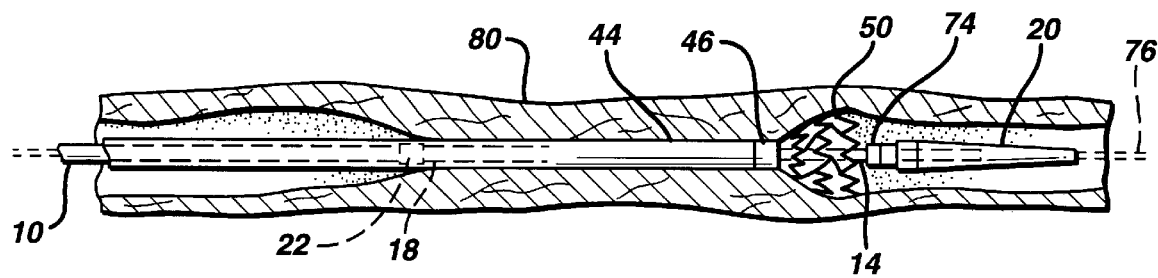
Figure 9:
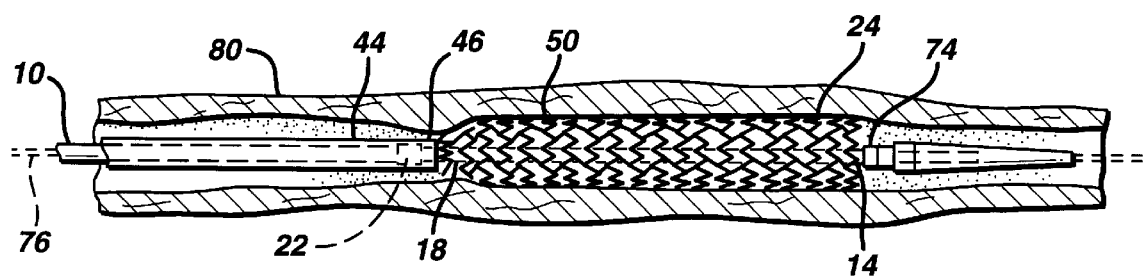

The method under which apparatus 1 deploys stent 50 can best be described by referring to FIGS. 7–10. In FIG. 7, the apparatus 1 has been inserted into a vessel 80 so that so that the stent bed 24 is at a target diseased site. Once the physician determines that the distal marker 74 and proximal marker 22 on shaft 10 indicating the ends of stent 50 are sufficiently placed about the target disease site, the physician would open Tuohy Borst valve 60. The physician would then grasp the proximal end 12 or proximal hub 5 of shaft 10 so as to hold shaft 10 in a fixed position. Thereafter, the physician would grasp the Tuohy valve 60 attached proximally to outer sheath 40 and slide it proximal, relative to the shaft 10 as shown in FIGS. 8 and 9. Stop 22 prevents the stent 50 from sliding back with sheath 40, so that as the sheath 40 is moved back, the stent 50 is effectively pushed out of the distal end 44 of the sheath 40. Stent 50 should be deployed in a distal to proximal direction to minimize the potential for creating emboli with the diseased vessel 80.

Figure 10:
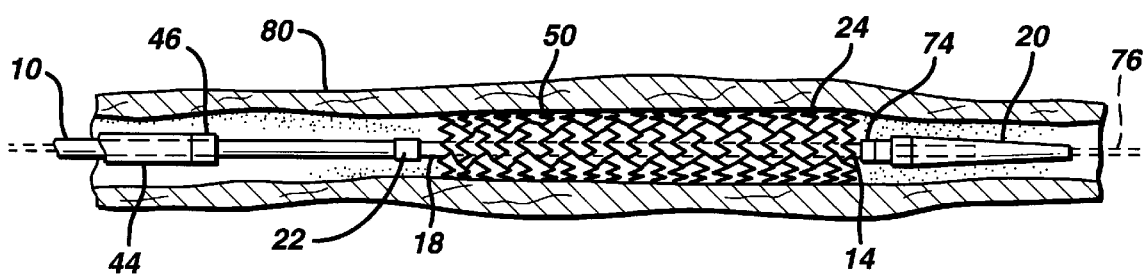

Stent deployment is complete when the radiopaque band 46 on the sheath 40 is proximal to radiopaque stop 22, as shown in FIG. 10. The apparatus 1 can now be withdrawn through stent 50 and removed from the patient.

Figure 5:
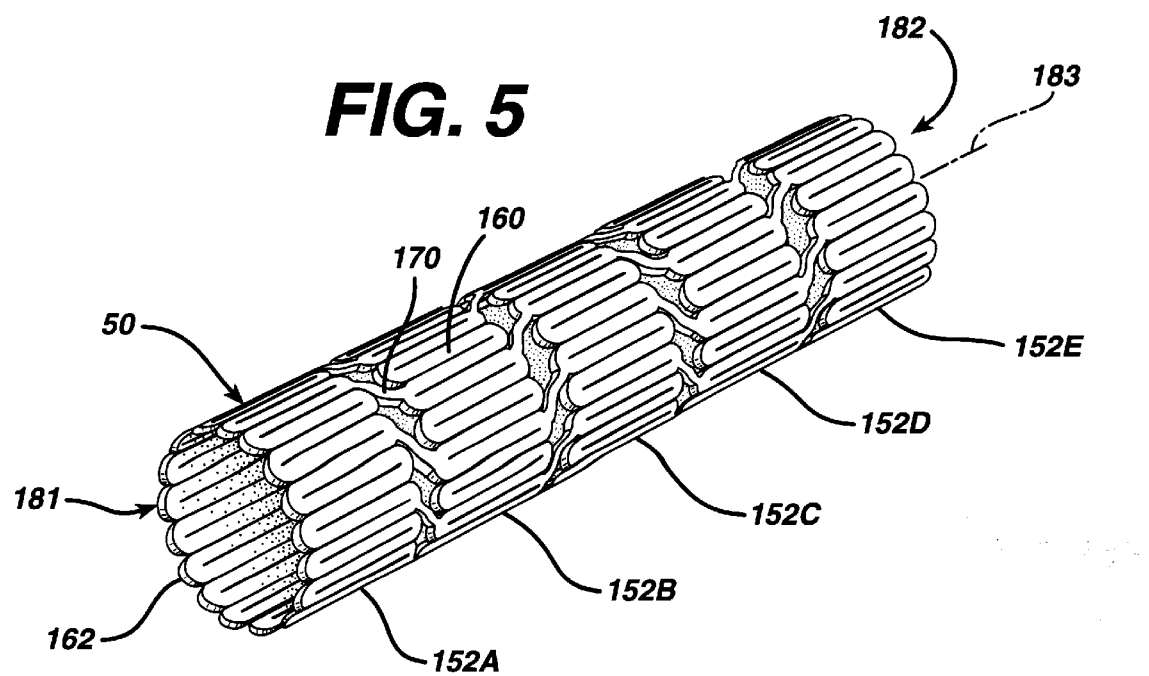
FIG. 5 is a perspective view of the constrained self expanding stent.

FIG. 5 shows a preferred embodiment of a stent 50 which can be used with the present invention. Stent 50 is shown in its un-expanded compressed state, before it is deployed. Stent 50 is preferably made from a superelastic alloy such as Nitinol. Most preferably, stent 50 is made from an alloy comprising from about 50.5% (as used herein these percentages refer to atomic percentages) Ni to about 60% Ni, and most preferably about 55% Ni, with the remainder of the alloy Ti. Preferably, the stent is such that it is superelastic at body temperature, and preferably has an Af in the range from about 24° C. to about 37° C. The superelastic design of the stent makes it crush recoverable which, as discussed above, can be used as a stent or frame for any number of vascular devices for different applications.

Stent 50 is a tubular member having front and back open ends 181 and 182 and a longitudinal axis 183 extending therebetween. The tubular member has a first smaller diameter, FIG. 5, for insertion into a patient and navigation through the vessels, and a second larger diameter, FIGS. 8–10, for deployment into the target area of a vessel. The tubular member is made from a plurality of adjacent hoops 152, FIG. 5 showing hoops 152(*a*)–152(*e*), extending between the front and back ends 181 and 182. The hoops 152 include a plurality of longitudinal struts 160 and a plurality of loops 162 connecting adjacent struts, wherein adjacent struts are connected at opposite ends so as to form an S or Z shape pattern. Stent 50 further includes a plurality of curved bridges 170 which connect adjacent hoops 152. Bridges 170 connect adjacent struts together at bridge to loop connection points which are offset from the center of a loop.

The above described geometry helps to better distribute strain throughout the stent, prevents metal to metal contact when the stent is bent, and minimizes the opening size between the features, struts, loops and bridges. The number of and nature of the design of the struts, loops and bridges are important factors when determining the working properties and fatigue life properties of the stent. Preferably, each hoop has between 24 to 36 or more struts. Preferably the stent has a ratio of number of struts per hoop to strut length (in inches) which is greater than 200. The length of a strut is measured in its compressed state parallel to the longitudinal axis of the stent.

In trying to minimize the maximum strain experienced by features, the present invention utilizes structural geometry's which distribute strain to areas of the stent which are less susceptible to failure than others. For example, one vulnerable area of the stent is the inside radius of the connecting loops. The connecting loops undergo the most deformation of all the stent features. The inside radius of the loop would normally be the area with the highest level of strain on the stent. This area is also critical in that it is usually the smallest radius on the stent. Stress concentrations are generally controlled or minimized by maintaining the largest radii possible. Similarly, we want to minimize local strain concentrations on the bridge and bridge to loop connection points. One way to accomplish this is to utilize the largest possible radii while maintaining feature widths which are consistent with applied forces. Another consideration is to minimize the maximum open area of the stent. Efficient utilization of the original tube from which the stent is cut increases stent strength and it's ability to trap embolic material.

Although particular embodiments of the present invention have been shown and described, modification may be made to the device and/or method without departing from the spirit and scope of the present invention. The terms used in describing the invention are used in their descriptive sense and not as terms of limitations.

That which is claimed is:

1. A delivery apparatus for a self-expanding stent, said apparatus comprising:
   a) an outer sheath, comprising an elongated tubular member having distal and proximal ends, said outer sheath comprising an outer polymeric layer, and inner polymeric layer, and a wire reinforcing layer between said inner and outer layers, said reinforcing layer being more rigid than said inner and outer layers;
   b) an inner shaft located coaxially within said outer sheath, said shaft having a distal end, extending distal to said distal end of said sheath, and a proximal end, extending proximal to said proximal end of said sheath, said shaft further including a stop attached thereto, said stop being proximal to said distal end of said sheath; and
   c) a self-expanding superelastic nickel-titanium alloy stent located within said sheath, said stent making frictional contact with and exerting an outward force on said inner layer of said sheath, said stent located between said stop and said distal end of said sheath with a portion of said shaft disposed coaxially within a lumen of said stent, said stent makes contact with said stop during deployment of said stent.

2. The apparatus of claim 1 wherein said wire reinforcing layer comprises braids of metallic wire.

3. The apparatus of claim 2 wherein said wire comprises stainless steel.

4. The apparatus of claim 1 wherein said wire reinforcing layer comprises a metallic coil.

5. The apparatus of claim 1 wherein said braided reinforcing layer extends along a predetermined of length of a distal portion of said outer shaft.

6. The apparatus of claim 1 wherein said stop makes no substantial frictional contact with said outer sheath.

7. The apparatus of claim 1 wherein said shaft has a proximal portion made from a metallic material.

8. The apparatus of claim 7 wherein said proximal portion is made from material selected from a group comprising: stainless steel, nickel titanium alloys.

9. The apparatus of claim 1 wherein said shaft further includes a distal tip, said distal tip has a proximal end having an outer diameter which is not less than an outer diameter of said sheath.

10. The apparatus of claim 9 wherein said distal tip of said shaft is radiopaque.

11. The apparatus of claim 1 wherein said stop is radiopaque.

12. The apparatus of claim 11 wherein said distal end of said sheath is radiopaque.

13. The apparatus of claim 1 wherein said shaft has an increasing durometer along its length from its distal end to its proximal end.

14. The apparatus of claim 1 wherein said shaft further includes a reinforcing sleeve extending along a predetermined length of said shaft proximal to said stop.

15. A delivery apparatus for a self-expanding stent, said apparatus comprising:
   a) an outer sheath, comprising an elongated tubular member having distal and proximal ends, said outer sheath comprising an outer polymeric layer, and inner polymeric layer, and a braided metallic wire reinforcing layer between said inner and outer layers, said reinforcing layer being more rigid than said inner and outer layers;
   b) an inner shaft located coaxially within said outer sheath, said shaft having a distal end, extending distal to said distal end of said sheath, and a proximal end, extending proximal to said proximal end of said sheath, said shaft further including a stop attached thereto, said stop being proximal to said distal end of said sheath; and
   c) a self-expanding superelastic nickel-titanium alloy stent located within said sheath, said stent making frictional contact with and exerting an outward force on said inner layer of said sheath, said stent located between said stop and said distal end of said sheath with a portion of said shaft disposed coaxially within a lumen of said stent, said stent makes contact with said stop during deployment of said stent.

16. The apparatus of claim 15 wherein said braided metallic wire reinforcing layer comprises stainless steel.

17. The apparatus of claim 15 wherein said braided reinforcing layer extends along a predetermined of length of a distal portion of said shaft.

18. The apparatus of claim 15 wherein said stop makes no substantial frictional contact with said outer sheath.

19. The apparatus of claim 15 wherein said shaft has a proximal portion made from a metallic material selected from a group comprising: stainless steel, nickel titanium alloys.

20. The apparatus of claim 15 wherein said stent is made from a superelastic nickel-titanium alloy.

21. The apparatus of claim 15 wherein said distal tip includes a radiopaque marker disposed thereon.

22. The apparatus of claim 15 wherein said stop is radiopaque.

23. The apparatus of claim 22 wherein said distal end of said sheath has a radiopaque marker disposed thereon.

24. The apparatus of claim 15 wherein said shaft has an increasing durometer along its length from its distal end to its proximal end.

25. The apparatus of claim 15 wherein said shaft further includes a reinforcing sleeve extending along a predetermined length of said shaft proximal to said stop.

26. A delivery apparatus for a self-expanding stent, said comprising:
   a) an outer sheath, comprising an elongated tubular member having distal and proximal ends, said outer sheath comprising an outer polymeric layer, and inner polymeric layer, and a braided metallic wire reinforcing layer between said inner and outer layers, said reinforcing layer being more rigid than said inner and outer layers, said sheath having a plurality of sections having increasing durometers from its distal end to its proximal end, said sheath having a radiopaque marker disposed at its distal end;
   b) an inner shaft located coaxially within said outer sheath, said shaft having a distal end, extending distal to said distal end of said sheath, and a proximal end, extending proximal to said proximal end of said sheath, said shaft having a radiopaque stop attached thereto, said stop being proximal to said distal end of said sheath, said shaft further including a distal tip, said distal tip having a proximal end having an outer diameter which is not less than an outer diameter of said sheath, said tip having a radiopaque marker disposed thereon; and c) a self-expanding superelastic nickel-titanium alloy located within said sheath, said stent making frictional contact with and exerting an outward force on said inner layer of said sheath, said stent located between said stop and said distal end of said sheath with a portion of said shaft disposed coaxially within a lumen of said stent, said stent makes contact with said stop during deployment of said stent.

27. The apparatus of claim 26 wherein said braided metallic wire reinforcing layer comprises stainless steel.

28. The apparatus of claim 26 wherein said braided reinforcing layer extends along a predetermined of length of a distal portion of said shaft.

29. The apparatus of claim 26 wherein said stop makes no substantial frictional contact with said outer sheath.

30. The apparatus of claim 26 wherein said shaft has a proximal portion made from a metallic material selected from a group comprising: stainless steel, nickel titanium alloys.

31. The apparatus of claim 26 wherein said shaft further includes a reinforcing sleeve extending along a predetermined length of said shaft proximal to said stop.

* * * * *

UNITED STATES PATENT AND TRADEMARK OFFICE
CERTIFICATE OF CORRECTION

PATENT NO. : 6,019,778
DATED : February 1, 2000
INVENTOR(S) : Wilson, et al.

It is certified that error appears in the above-indentified patent and that said Letters Patent is hereby corrected as shown below:

Col. 10, line 45, insert --apparatus-- after said

Col. 11, line 1, insert --stent-- after alloy

Signed and Sealed this

Fourteenth Day of November, 2000

Attest:

Q. TODD DICKINSON

*Attesting Officer*      *Director of Patents and Trademarks*